United States Patent [19]

Liu

[11] Patent Number: 4,941,899

[45] Date of Patent: Jul. 17, 1990

[54] CYCLONE PERSONAL SAMPLER FOR AEROSOLS

[75] Inventor: Benjamin Y. H. Liu, North Oaks, Minn.

[73] Assignee: Regents of the University of Minnesota, Minneapolis, Minn.

[21] Appl. No.: 342,479

[22] Filed: Apr. 24, 1989

[51] Int. Cl.$^5$ .................... B01D 53/24; G01N 1/24
[52] U.S. Cl. ........................ 55/270; 55/337; 55/356; 55/429; 73/863.23
[58] Field of Search ............... 55/270, 336, 337, 356, 55/429; 73/863.22, 863.23, 863.25, 864.71

[56] References Cited

U.S. PATENT DOCUMENTS

| | | | |
|---|---|---|---|
| 3,686,835 | 8/1972 | Strange et al. | 55/270 |
| 3,748,905 | 7/1973 | Fletcher et al. | 73/863.25 |
| 3,802,167 | 4/1974 | Turman | 55/270 X |
| 3,823,602 | 7/1974 | Anderson | 55/270 X |
| 3,920,426 | 11/1975 | Tu et al. | 55/337 |
| 3,957,469 | 5/1976 | Nebash | 73/863.22 |
| 4,178,794 | 12/1979 | Jugle et al. | 55/270 X |
| 4,274,846 | 6/1981 | Smith | 55/270 |
| 4,544,386 | 10/1985 | Trayford, III et al. | 55/270 |
| 4,713,095 | 12/1987 | Ricciardelli | 55/270 X |
| 4,796,475 | 1/1989 | Marpel | 55/270 X |
| 4,827,779 | 5/1989 | Marple et al. | 73/863.22 |

FOREIGN PATENT DOCUMENTS 927271 5/1963 United Kingdom ............... 55/270

OTHER PUBLICATIONS

Thomas Tomb et al., "A New Two-Stage Respirable Dust Sampler", American Industrial Hygiene Assoc. Journal, vol. 36, #1, Jan. 1975, pp. 1-9.
T-868,006, J.B. Shutack, Defensive Publication, Nov. 18, 1969.
Rubow, K. L., B. K. Cantrell and V. A. Marple, "Measurement of Coal Dust and Diesel Aerosols in Underground Minds", *Proceedings of the VIIth International Pneumoconioses Conference*, Pittsburgh, PA, Aug. 23-26, 1988.
Cantrell, B. K. and K. L. Rubow, "Mineral Dust and Diesel Exhaust Aerosols in Underground Metal and Nonmetal Mines", *Proceedings of the VIIth International Pneumoconioses Conference*, Pittsburgh, PA, Aug. 23-26, 1988.

Primary Examiner—Robert Spitzer
Attorney, Agent, or Firm—Kinney & Lange

[57] ABSTRACT

A cyclone type personal aerosol sampler has a two-stage operation with a standard cyclone sampler providing a cutoff of particles in the range of 10 microns to a secondary cyclone sampler. The secondary cyclone sampler has the ability to inertially separate out particles below about 0.8 microns from larger particles. The secondary sampler has a readily removable cup for collecting the larger particles, and an easily replaceable filter for collecting the smaller particles for analysis.

10 Claims, 1 Drawing Sheet

U.S. Patent    Jul. 17, 1990    4,941,899
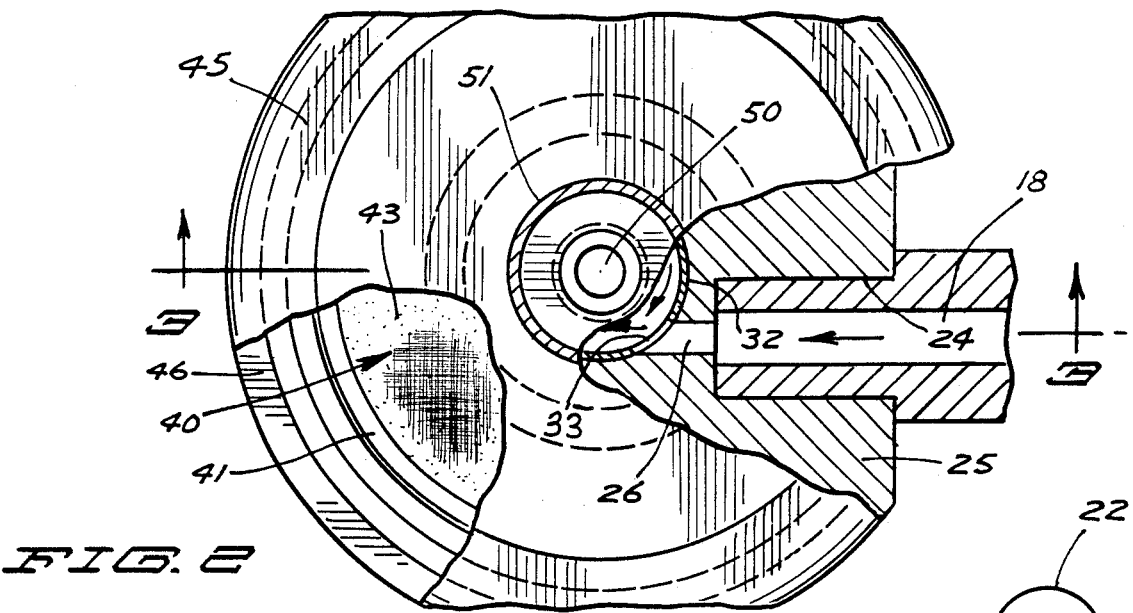
FIG. 2
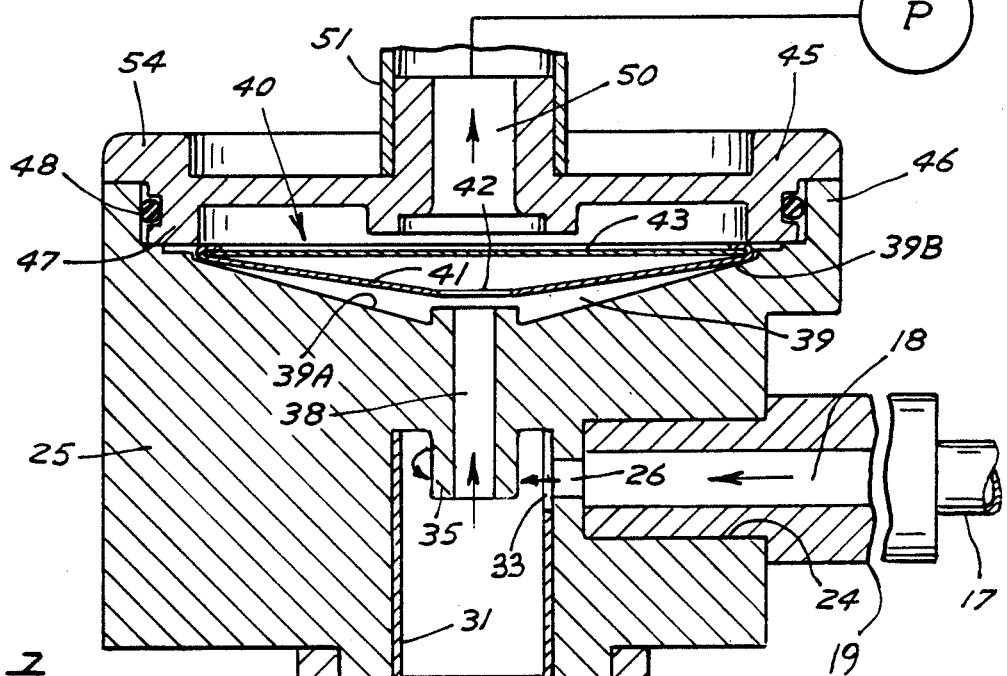
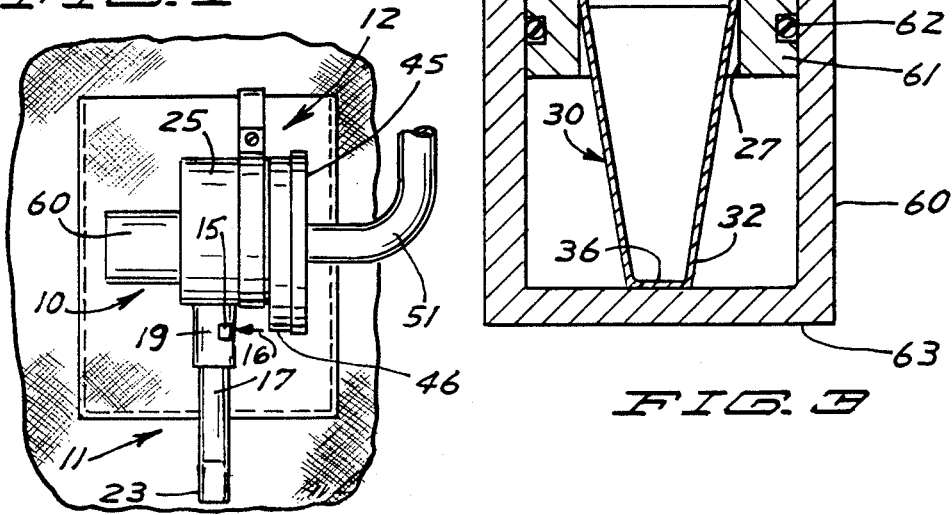
FIG. 1
FIG. 3

CYCLONE PERSONAL SAMPLER FOR AEROSOLS

BACKGROUND OF THE INVENTION

1. Field of the Invention.

The present invention relates to cyclonetype, personal samplers for use for detecting aerosols, in particular, samplers that are used to determine the amount of diesel exhaust aerosols and coal dust aerosols in underground mines.

2. Description of the Prior Art.

Substantial work has been carried out in relation to the effects of respirating diesel exhaust particles, and research has suggested that exposure to diesel exhaust particulate matter may have adverse health effects.

Sampling methods have been undertaken for the measurement of diesel aerosols and underground coal mines, as well as sampling coal dust particles. The diesel exhaust particles are generally quite small, and by providing a cut-off size, evaluations of the amount of coal dust particles and diesel exhaust particles can be made. The U.S. Bureau of Mines and the University of Minnesota have undertaken various experiments, and a paper by Kenneth L. Rubow, Bruce K. Cantrell, and Virgil A. Marple, entitled "Measurement of Coal Dust and Diesel Exhaust Aerosols in Underground Mines," has been prepared. A second paper was also prepared in cooperation between the U.S. Bureau of Mines and the University of Minnesota, prepared by Bruce Cantrell and Kenneth L. Rubow, entitled "Mineral Dust and Diesel Exhaust Aerosols Measurements in Underground Metal and Non-metal Mines," which deals with evaluating sampling methods for measuring diesel aerosol in underground mines As the requirements of the environmental agencies of various governments become more definite, there is seen a need for very reliably determining presence of aerosols which are harmful, including diesel exhaust aerosols and coal dust.

SUMMARY OF THE INVENTION

The present invention relates to a personal sampler, that is one which is of sufficiently small size so that it can be worn by a user to determine the quality of air being respirated, which utilizes a two-stage cyclone evaluator that includes a conventional elongated personal cyclone separator that has a lower cut-off size of in the range of 10 microns. The output of fluid containing particles less than 10 microns is provided to the inlet of a collector-separator that provides for separation between particles at about 0.8 microns, and provides convenient receptacles or filters for collection of the two different size particles.

In order to do this, the secondary cyclone separator is designed to provide a flow that circulates in a chamber to deposit particles that are larger than 0.8 microns, and generate a vortex that will carry the 0.8 micron and smaller particles in a flow across a filter element to trap such particles. A personal sampling pump of conventional design is used for providing the necessary air flow in a conventional manner.

Further, the secondary cyclone includes quickly and conveniently replaceable collection elements that are held in place with conveniently removable retainer housings, so that the personal sampling cyclone can be disassembled and the collection elements removed without disturbing or in any way altering the collection information.

The device has few moving parts, and can be readily adapted to use cartridge-type filters and collector housings for the two batches of particle size segregated materials to be collected.

The unit can conveniently clip onto a shirt pocket or other exterior portions of clothing of a wearer for use.

BRIEF DESCRIPTION OF THE DRAWINGS

FIG. 1 is a schematic representation of a personal sampling cyclone made according to the present invention shown clipped to a shirt pocket;

FIG. 2 is a side elevational view of the device of FIG. 1 with parts in section and parts broken away; and FIG. 3 is a sectional view taken as on line 3—3 in FIG. 2.

DETAILED DESCRIPTION OF THE PREFERRED EMBODIMENTS

A cyclone-type personal aerosol sampler, made according to the present invention, is illustrated generally at 10, and includes a conventional, cylindrical, upright cyclone sampler indicated generally at 11, which is coupled in series with a secondary cyclone sampler for collecting and controlling the aerosols to be investigated and which is indicated generally at 12. This secondary cyclone sampler is made according to improvements of the present invention. The cylindrical, conventional cyclone sampler (a Dorr-Oliver cyclone) has an inlet 15 for receiving incoming air as indicated by the arrow 16 in FIG. 1, and the inlet is offset from the central axis of the cylindrical body 17 so that there is a spiralling of air that is then drawn through the body 17 toward an outlet passageway 18 defined in an outlet tube 19 that opens to the interior passage of the cyclone body 17. This cyclone separator is, again, conventional, and the flow of air inwardly, as indicated by the arrow 16, is controlled by the outward flow from the secondary cyclone sampler 12. Such flow is generated by a small air pump 22 which is shown schematically, and which is known in the field. Such air pumps are used for various personal aerosol samplers. It can comprise a battery powered pump that draws a desired volume of air through the personal sampling assembly 10 to create the necessary flow for inertial separation of particles, first at the vertically oriented cylindrical body 17, and then, secondly, in the secondary cyclone sampler 12. The larger particles collected in the body 17 can be removed by removing an end cap 23 at the bottom of the body 17.

The outlet tube 19 is fitted into a socket 24 defined in a secondary cyclone housing 25 that forms the main body for the secondary cyclone 12. The socket 24 opens to an inlet bore 26 which enters a cyclone chamber 27 defined in the housing 25. The chamber is a bore that is of size to receive a cup-type receptacle 30 that has an upper cylindrical end 31 fitting into the bore 27, and a lower tapered end 32 that extends out from the outer end of the bore 27 a selected distance. The cylindrical cup 31 has a slot indicated at 33, defined therein which aligns with the inlet bore 26, so that air flowing in from the standard cyclone 17 can enter the interior of the cup, which forms an inner wall of the cyclone chamber when it is in place.

Flow through the bore 26, as shown, enters tangentially to the wall of the cylindrical cup portion 31 and the fluid flowing in then tends to circulate around the wall 31 to form the cyclone-type separator. As it circulates around, it forms a vortex in the central portions A vortex finder sleeve 35 is formed at the inner end of the chamber 27, to form an annular passageway around the vortex finder sleeve so that the air will move in a cyclonic action.

The particles that are larger than a selected size will be deposited onto the interior surfaces of the cone shaped section 32, which has a closed lower wall 36, so that these particles will be collected. The vortex finder has a central outlet passageway 38 that leads into a filter compartment or chamber 39 at the opposite end of the body 25 from the bore 27. The filter chamber is formed with an outwardly tapered surface 39A, and at its outer ends this forms an annular edge support surface 39B for supporting a filter assembly 40 in place. The filter assembly 40, as shown, has a thin metal (aluminum foil) shallow cone-shaped backing 41, and a paper filter 43 stretched across and retained at the open end of the backing 41. The backing 41 has a central opening 42 that aligns with the bore 38 so that air coming through the vortex finder opening 38 will then have to pass through the filter before it exits. A filter retainer-cap 45 is fitted inside an annular flange 46 on the body 25, and the cap 45 has a neck 47 that carries an O-ring 48 that forms a friction seal around the interior surface of the neck 46 when the filter cap is put into place. As shown, the filter cap is closed except for a central outlet passageway 50 that is connected with a suitable tube 51 to the pump 22.

The cap 45 has an outer flange 54 which can be manually held for removing the cap from the housing 25 and then removing the filter assembly after a collection period has expired.

The small particles that are collected on the filter 43 are generally less than 0.8 microns, and these are the particles that are carried with the vortex through the openings 38 and 42 and then collected on the filter 43.

The collection cup 30 for particles which are between the size of particles separated out by the standard cyclone separator 17 and about 0.8 microns, is retained in place through the use of a removable O-ring friction-fit cap 60 that fits around a neck 61 formed in the end of the housing 25 opposite from the chamber 39. The neck 61 has an O-ring groove holding an O-ring 62 therein so that friction engagement of the inner surface of the side wall of the cap 60 is made. The cap 60 has an end wall 63 which bears against the wall 36 and holds the collection cup 30 in position for collecting the particles that are separated out by the cyclonic action that occurs in the cylindrical wall portion of the cup 30.

The cutoff can be selectively sized for the standard cyclone 17, that is, the upper size of the particles that will be permitted to exit from this cyclone sample can be changed so it conforms to a respirable particle cut curve which can vary with different types of materials. Generally the particles that are considered harmful are below 10 microns. The cut size curves for various particles are standard and available. Therefore, for purposes of discussion, the cutoff point will be considered to be 10 microns. Particles smaller than 10 microns will than enter through the opening passageway 26 into the cyclone chamber formed by the interior surface of the cylindrical end portion 31 of cup 30, and the cyclonic action forming the vortex that passes out through the bore 38 of the vortex finder 35 will be selected to collect particles larger than in the range of 0.8 microns in the cup. The particles that are a size in between 0.8 microns and 10 microns, will fall to the bottom collection portion 32 of the cup 30 and be collected there during the time that the personal sampler or collector is being operated.

The smaller particles are then carried up with the flow through the bore 38, through opening 42, and as the flow passes through paper filter 43 that closes the opening leading from the housing or body 25, the small particles are collected on the filter.

The filter 43 and its support backing 41 can be laid into place, after the cap 45 has been removed. The cap 45 can be reinserted and held in with a friction force that can be of a desired level which is provided by the O-ring 48. This frictional force will hold the filter paper positively in position so that it will not be easily dislodged during use. The cap can easily be removed and the filter can be removed without dislodging the particles or losing any of the particles that have been collected.

The same is true with the collection cup 30, in that it is held in position with an easily removable cap 60 that is frictionally held through the O-ring 62, and once the cap 60 is taken off, the cup 30 can be removed, sealed and stored until it is taken to another location for analysis.

A two-stage sampler is thus provided which can separate out the respirable particles into particles that are attributable primarily to coal dust, that is, those between 0.8 and 10 microns, and separately collect particles that are under 0.8 microns and relate primarily to diesel exhaust particles. The quality of air in the environment, therefore, can be measured, and when such sampler is worn by a person in an underground mine, a warning as to when air quality is deteriorating to a point of being hazardous can be determined.

Although the present invention has been described with reference to preferred embodiments, workers skilled in the art will recognize that changes may be made in form and detail without departing from the spirit and scope of the invention.

What is claimed is:

1. A personal particle sampler of size to be worn on a shirt pocket or the like for providing information relating to concentration of particles that are below a primary cutoff size comprising a housing, an inlet for atmospheric air, a vortex forming chamber in said housing for forming a vortex of air entering the housing through the inlet, said chamber including a removable section comprising a cup slidably mounted in a bore in the housing and having an enclosed wall and an end spaced from the inlet, an outlet in an end of said chamber adjacent the inlet for outlet flow from the vortex formed, the vortex action depositing particles above a secondary cutoff size in the cup, and filter means to filter the flow from the outlet to collect particles on the filter means.

2. A personal particle sampler according to claim 1, wherein the cup is removably mounted to the housing at a first end thereof, and a friction fit cover enclosing the cup and sealing the chamber, the cover being removable to permit removing the cup.

3. The personal particle sampler according to claim 1, wherein said enclosed wall of said cup has a cylindrical section that forms a liner in said bore to form the chamber, said inlet opening being defined through the wall forming said cylindrical section of said cup so that the vortex is formed entirely within said removable cup, said cup having a remote section in which the particles separated by the vortex action are deposited, the remote section having the end wall thereon.

4. The personal particle sampler according to claim 1, including a tandem arrangement of cyclone separators, and a primary cyclone separator providing a primary cutoff size and having an outlet coupled to the inlet of the chamber and housing of claim 1.

5. The personal particle sampler according to claim 4, wherein the vortex forming chamber includes a tubular sleeve formed on the housing and extending inwardly into a portion of the chamber and aligned with the inlet opening, so that the air tends to move around the sleeve to form the vortex action, the sleeve having the outlet defined through the center thereof.

6. The personal particle sampler of claim 1, wherein said housing includes a filter chamber at an opposite end thereof from said cup, said cup being positioned to be on the lower side of said housing when the personal sampling impactor is being worn by a person, said filter means comprising a paper filter supported across an outlet of the filter chamber, said paper filter being held in place with a frictionally held cover retaining the cover, said cover being removable for removing of the filter means.

7. The personal particle sampler of claim 6, wherein said cover has an outlet opening connected to a personal particle sampler pump that provides a flow through said personal particle sampler.

8. A personal particle sampler for providing information relating to concentration of particles that are below a primary cutoff size comprising a housing of size to be worn by a person, a bore formed in the housing comprising a vortex forming chamber open at one remote end of the chamber, a vortex finder sleeve formed in the housing at an inlet end of the bore forming the chamber, an inlet opening on a side of said chamber aligned with the vortex finder sleeve to form a cyclonic action around the vortex finder sleeve as air flows from the inlet into the chamber, an outlet formed in the center of the vortex finder sleeve for outlet flow from the vortex formed, a cup removably slidably mounted in the bore and having an enclosed cylindrical wall section that forms a liner in the chamber surrounding the vortex finder sleeve, and said cup having a remote end that extends out of the bore of the housing, said inlet opening extending through a wall forming said cylindrical wall section of said cup so that the vortex is formed entirely within said cup, said cup remote end being closed to collect the particles separated by cyclonic action, the cyclonic action depositing particles above a secondary cutoff size in the cup, and means to removably retain the cup in the bore.

9. The personal particle sampler of claim 8 and a cover member engaging the cup and sealing the chamber, the cover member being frictionally maintained on said housing to retain the cup and easily removable to permit removing the cup from the bore.

10. The personal particle sampler according to claim 8, and removable filter means positioned on the housing to filter the flow from the outlet to collect particles passing through the outlet of the chamber.

* * * * *